(12) United States Patent
Biffi et al.

(10) Patent No.: US 11,690,867 B2
(45) Date of Patent: Jul. 4, 2023

(54) LIQUID COMPOSITION FOR USE IN THE TREATMENT OF GASTROESOPHAGEAL REFLUX

(71) Applicant: SOFAR SWISS SA, Lugano (CH)

(72) Inventors: Andrea Biffi, Lugano (CH); Sara Sala, Lugano (CH)

(73) Assignee: SOFAR SWISS SA, Lugano (CH)

( * ) Notice: Subject to any disclaimer, the term of this patent is extended or adjusted under 35 U.S.C. 154(b) by 0 days.

(21) Appl. No.: 17/743,362

(22) Filed: May 12, 2022

(65) Prior Publication Data

US 2022/0265701 A1     Aug. 25, 2022

Related U.S. Application Data

(62) Division of application No. 16/340,813, filed as application No. PCT/IB2017/056254 on Oct. 10, 2017, now Pat. No. 11,337,992.

(30) Foreign Application Priority Data

Oct. 10, 2016   (IT) .................. 102016000101413

(51) Int. Cl.
| | |
|---|---|
| A61K 31/728 | (2006.01) |
| A61P 1/04 | (2006.01) |
| A61K 31/726 | (2006.01) |
| A61K 35/644 | (2015.01) |
| A61K 36/886 | (2006.01) |
| A61K 31/737 | (2006.01) |

(52) U.S. Cl.
CPC .......... *A61K 31/728* (2013.01); *A61K 31/726* (2013.01); *A61K 31/737* (2013.01); *A61K 35/644* (2013.01); *A61K 36/886* (2013.01); *A61P 1/04* (2018.01)

(58) Field of Classification Search
CPC .............. A61K 2300/00; A61K 31/728; A61K 35/644; A61K 31/737; A61K 36/886; A61K 31/726; A61P 1/04
See application file for complete search history.

(56) References Cited

U.S. PATENT DOCUMENTS

| | | | |
|---|---|---|---|
| 5,178,878 A | 1/1993 | Wehling et al. | |
| 9,006,207 B2 | 4/2015 | Ng et al. | |
| 2004/0146993 A1 | 7/2004 | Khare et al. | |
| 2006/0147522 A1 | 7/2006 | Olmstead et al. | |
| 2009/0208588 A1 | 8/2009 | Brown | |
| 2009/0252709 A1 | 10/2009 | Nose et al. | |
| 2011/0038945 A1 | 2/2011 | Gear | |
| 2011/0071106 A1 | 3/2011 | Pizzoni | |
| 2011/0097401 A1 | 4/2011 | Phillips et al. | |
| 2011/0159104 A1 | 6/2011 | Teslenko | |
| 2015/0164859 A1 | 6/2015 | Chollet et al. | |
| 2015/0284478 A1 | 10/2015 | Agar et al. | |
| 2019/0125664 A1 | 5/2019 | Biffi | |
| 2019/0125665 A1 | 5/2019 | Biffi | |
| 2019/0262388 A1 | 8/2019 | Biffi et al. | |

FOREIGN PATENT DOCUMENTS

| | | |
|---|---|---|
| EP | 2 581 090 A1 | 4/2013 |
| JP | 61-47418 A | 3/1986 |
| WO | 2010/136872 A2 | 12/2010 |
| WO | 2017/055909 A1 | 4/2017 |

OTHER PUBLICATIONS

Boarino et al., "Symptomatic response to GERDOFF® in patients with gastro-esophageal reflux disease and poor response to alginates: an exploratory, post-market, open-label study," *Turk J Gastroenterol* 31(6):466-473, 2020.
ChemIDplus, "Substance Name: Hyaluronic Acid [BAN]," Registry No. 9004-61-9, Feb. 12, 2022, (2 pages).
Claire, "Reflux and natural remedies: Aloe Vera and Manuka Honey," Peptest, Aug. 24, 2016, URL=https://www.peptest.co.uk/reflux-and-natural-remedies-aloe-vera-and-manuka-honey/. (4 pages).
International Search Report and Written Opinion, dated Jan. 26, 2018, for International Application No. PCT/IB2017/056254. (12 pages).
Italian Search Report and Written Opinion, dated Jun. 19, 2018, for Italian Application No. IT201700124424. (14 pages).
Italian Search Report and Written Opinion, dated Jun. 20, 2018, for Italian Application No. IT201700124434. (9 pages).

(Continued)

*Primary Examiner* — Aaron J Kosar
(74) *Attorney, Agent, or Firm* — Seed IP Law Group LLP

(57) ABSTRACT

The present invention relates to a liquid composition for use in the treatment of gastroesophageal reflux. The composition of the present invention comprises a mixture which comprises or, alternatively, consists of a combination of *Aloe vera* gel, hyaluronic acid and honey and, optionally, food or pharmaceutical grade additives and/or technological excipients. The composition of the present invention also relates to a medical device comprising a mixture which comprises or, alternatively, consists of a combination of *Aloe vera* gel, hyaluronic acid and honey and, optionally, food or pharmaceutical grade additives and/or technological excipients. Said composition or composition for a medical device being for use in the preventive and/or curative treatment of the symptoms associated with gastroesophageal reflux and the disease caused thereby, as well as for use in the preventive and/or curative treatment of gastroesophageal reflux disorders.

20 Claims, No Drawings

(56) References Cited

OTHER PUBLICATIONS

Palmieri et al., "Preliminary clinical experience with a new natural compound in the treatment of oesophagitis and gastritis: symptomatic effect," *Trends in Medicine* 9(4):219-225, 2009.

Palmieri et al., "Fixed combination of hyaluronic acid and chondroitin-sulphate oral formulation in a randomized double blind, placebo controlled study for the treatment of symptoms in patients with non-erosive gastroesophageal reflux," *European Review for Medical and Pharmacological Sciences* 7 7:3272-3278, 2013.

Popescu, "Why Oral Disintegrating Tablets?," *ONdrugDelivery Magazine* (69):35-38, 2016.

Smart et al., "Comparison of a dimethicone/antacid (Asilone gel) with an alginate/antacid (Gaviscon liquid) in the management of reflux oesophagitis," *Journal of the Royal Society of Medicine* 53:554-556, 1990.

Song et al., "The Relationship between Gastroesophageal Reflux Disease and Chronic Periodontitis," *Gut and Liver* 8(1):35-40, 2014.

"WHO monographs on selected medicinal plants: Aloe Vera Gel," *World Health Organization* 1:43-49, 1999. (10 pages).

LIQUID COMPOSITION FOR USE IN THE TREATMENT OF GASTROESOPHAGEAL REFLUX

CROSS-REFERENCES TO RELATED APPLICATIONS

This application is a divisional of U.S. application Ser. No. 16/340,813, filed Apr. 10, 2019, which is a national stage application of International Application No. PCT/IB2017/056254, filed Oct. 10, 2017, which claims the benefit of Italian Patent Application No. 102016000101413, filed Oct. 10, 2016, the contents of each of which are incorporated herein by reference in their entirety.

FIELD OF THE INVENTION

The present invention relates to a liquid composition for use in the treatment of gastroesophageal reflux, preferably an aqueous liquid composition. The composition of the present invention, preferably in the form of an aqueous liquid composition, comprises a mixture which comprises or, alternatively, consists of a combination of *Aloe vera* gel, hyaluronic acid and honey and, optionally, food or pharmaceutical grade additives and/or technological excipients. The composition of the present invention, preferably in the form of an aqueous liquid composition, also relates to a medical device comprising a mixture which comprises or, alternatively, consists of a combination of *Aloe vera* gel, hyaluronic acid and honey and, optionally, food or pharmaceutical grade additives and/or technological excipients. Said composition or composition for a medical device being for use in the preventive and/or curative treatment of the symptoms associated with gastroesophageal reflux and the disease caused thereby, as well as for use in the preventive and/or curative treatment of gastroesophageal reflux disorders.

BACKGROUND OF THE INVENTION

Gastroesophageal reflux, or GER, is a phenomenon characterised by the temporary upflow of stomach contents into the esophagus, without there necessarily being regurgitation or vomiting. The reflux is principally due to releases of the lower esophageal sphincter (LES), which can be due to insufficient pressure of the LES relative to an increase in abdominal pressure, or a progressive weakening of the closing pressure.

Gastroesophageal reflux disease, abbreviated as GERD (or GORD, gastro-oesophageal reflux disease), is a chronic disease of gastroenterological interest, which is linked to pathological complications of gastroesophageal reflux (GER) and consists in damage to the mucosa of the esophagus caused by gastric acid.

The most common symptoms of GERD are burning in the gastroesophageal area (retrosternal burning or pyrosis), acidic aftertaste, regurgitation and, more rarely, coughing, painful swallowing (dysphagia and odynophagia), angina-like chest pain, nausea and an increase in salivation (sialorrhoea).

In addition to a worsening in the quality of life and a difficulty in taking in food and beverages, GERD can bring about permanent damage to the esophagus, such as chronic inflammation and necrosis of the esophageal epithelium (esophagitis), ulcers, esophageal stenosis, Barrett's esophagus, which is a form of metaplasia characterised by a replacement of the squamous epithelium typical of the esophagus with a cylindrical epithelium, and tumours. Subjects with persistent symptoms of GERD are considered to be at high risk of developing adenocarcinoma of the distal tract of the esophagus.

An assessment of the damage to the esophageal mucosa is generally performed by means of endoscopic examinations, e.g. gastroscopy or pH-metry.

Therapy for GERD is currently based on some basic hygienic-dietetic rules (cessation of the use of tobacco and intake of alcoholic beverages) and the administration (for more or less extended periods) of drugs belonging to the classes of proton pump inhibitors (PPIs), which considerably inhibit acid production in the stomach and have replaced antihistamine drugs (anti-$H_2$). In order to obtain relief from the symptoms, antacids and alginate-based drugs can also be used.

However, the administration of these drugs can be ineffective in some subjects and can have side effects at the intestinal level (diarrhoea, flatulence, abdominal pain), skin eruptions, heart palpitations and an increase in osteoporosis and bone fragility in the case of long-term treatments.

The problem of providing a means for the treatment or prevention of the symptoms associated with gastroesophageal reflux, and of GERD, which may overcome the drawbacks of the prior art, in particular as regards side effects, has not been solved to date.

DETAILED DESCRIPTION OF THE INVENTION

In order to overcome said problem, the present invention provides a composition, comprising substances of natural origin, which is capable of treating (preventing and/or curing) the symptoms associated with gastroesophageal reflux, and the disease caused thereby, and which is practically devoid of the side effects that are present in the prior art treatments.

The present invention relates to a liquid composition (C) comprising a mixture which comprises or, alternatively, consists of a combination of the following substances:
 (a) *Aloe vera* gel; and
 (b) hyaluronic acid or a salt thereof; and
 (c) honey, and at least one excipient, or additive, suitable for pharmaceutical or food use.

Preferably, the liquid composition (C) is for use in the treatment of gastroesophageal reflux and is in the form of an aqueous liquid composition. It has been found that the administration of a mixture which comprises or, alternatively, consists of a combination of the three substances (a), (b) and (c) is capable of considerably decreasing/reducing and/or eliminating the symptoms and disorders associated with gastroesophageal reflux, alleviating the effects of the disease itself. Advantageously, the liquid composition (C) of the present invention acts along the esophagus and performs an anti-inflammatory and cicatrising action against the lesions caused to the mucosa as a result of the upflow of vapours and acidic substances or substances of an acidic character from the stomach towards the esophagus. In particular, the liquid composition (C) of the present invention enables better contact of the individual components/substances contained in the mixture with the oral-pharyngeal-laryngeal-esophageal wall and favours the protection, lubrication and repair thereof.

The composition (C) according to the present invention can be in the form of a clear solution (i.e. without precipitates) or suspension (i.e. a liquid phase that exhibits a visible opalescence, a solid suspended in a liquid or semi-liquid mass or a precipitate that can be suspended under stirring)

and it can be a dense viscous liquid (like caramel) or a flowable fluid (like water) or it can be a two-phase liquid/liquid system.

In a preferred embodiment, the composition of the present invention is in the form of a syrup, for example having a specific weight of about 1.2-1.3 kg/dm' at 20° C. and a viscosity of about 200-205 mPa·s at 20° C., comprising water and at least one food or pharmaceutical grade ingredient or additive and/or technological excipients.

In the context of the present invention, "treatment" means an intervention, comprising the administration of a substance, or mixture of substances or combination thereof, having the aim of eliminating, reducing/decreasing or preventing a pathology or disease and the symptoms or disorders associated therewith.

Unless specified otherwise, the contents of a component or substance in a composition refers to the percentage by weight of that component or substance relative to the total weight of the composition.

Unless specified otherwise, the indication that a composition "comprises" one or more components or substances means that other components or substances can be present in addition to the one or ones specifically indicated.

The composition of the present invention is to be understood as for either human or veterinary use, i.e. as a preparation to be applied to animals with the uses and methods known to the person skilled in the art.

In the context of the present invention, "treatment" means an intervention comprising the administration of a substance, or mixture of substances, having the aim of eliminating, reducing or preventing a pathology and the symptoms thereof.

In the context of the present invention, and in accordance with its common meaning, the term "honey" means the sweet natural product produced by bees (e.g. Apis mellifera) from the nectar of one or more plant varieties of any type or from secretions originating from living parts of plants or substances secreted by sucking insects that are found on living parts of plants, which they collect, transform, by combining them with specific substances of their own, deposit, dehydrate, store and leave in honeycombs to ripen and mature, according to the definition in Italian Legislative Decree no. 179 of 21 May 2004, transposing Directive 2001/110/EC relating to the production and marketing of honey. Said honey can be obtained through the standard processes known to the person skilled in the art (for example comprising extraction, separation, decanting, filtration, guided crystallisation and similar operations). In the context of the present invention, the term "honey" also comprises the products that can be obtained from natural honey, including those for industrial use, for example through refining processes or heat treatments, such as pasteurisation.

Patent EP 1 230 742 B1 describes the use of honey having a peroxide activity greater than 5 micrograms of hydrogen peroxide per gram of honey, in combination with crude food fibres (such as wheat bran), for the production of a composition for combating disorders such as gastroesophageal reflux.

As a non-limiting example, the honey usable in the composition of the present invention can have a pH between 3.5 and 4.5 (by weight relative to the total weight of the honey), a weight loss on drying of 18% and a content of reducing sugars in the dry product of 70%.

In the context of the present invention, "Aloe vera gel" means the generally colourless mucilaginous gel obtained from the parenchymatous tissue of the leaves of *Aloe vera* (L) Burm. f. or *Aloe barbadensis* Mill. *Aloe vera* gel does not have a use as a food substance or fibre and must not be confused with the juice, which is obtained from the same plant by incision and drying. In the monograph on *Aloe vera* gel in "WHO monographs on selected medicinal plants" (Vol. 1 World Health Organization, Geneva, 1999 pp. 43-49) it is stated that its principal components, besides water, are polysaccharides (pectins, hemicelluloses, glucomannans, acemannans and mannose derivatives) and that internal administration of *Aloe vera* gel has not been shown to have any significant therapeutic effect (pg. 45).

The present inventors have found, by contrast, that oral administration of *Aloe vera* gel, in combination with honey and hyaluronic acid, in accordance with the present invention, enables the symptoms and disorders associated with gastroesophageal reflux to be considerably decreased or completely eliminated.

Preferably, in the composition (C) of the present invention the *Aloe vera* gel is lyophilised inner leaf gel, more preferably from *Aloe barbadensis* Miller.

By way of non-limiting example, the *Aloe vera* gel used in the present invention can have a pH between 3 and 6, preferably between 3.5 and 5.5 or 3.7 and 4.2, and have a content of aloin lower than 1 ppm.

Hyaluronic acid is a non-sulphated glycosaminoglycan having an unbranched polysaccharide chain deriving from the condensation of disaccharide units which are formed, in turn, from residues of glucuronic acid and N-acetylglucosamine, linked together by alternating glycosidic bonds $\beta1\rightarrow4$ and $\beta1\rightarrow3$ (CAS number 9004-61-9).

Hyaluronic acid is widely used also in the form of a salt, for example as a sodium salt, via injections, in aesthetic surgery and dermatology, in otologic surgery, in ophthalmic surgery and in arthrology. Moreover, hyaluronic acid is widely used for topical application against inflammations or ulcerous lesions of the mouth and as a filler for skin applications in facial and body care products.

In the context of the present invention, the hyaluronic acid can be in the acid or salt form, for example as a sodium salt; the hyaluronic acid is preferably in linear form.

The mixture contained in the composition (C) according to the present invention may comprise hyaluronic acid, or salts thereof, having a different origin and various intervals of molecular weights.

The hyaluronic acid, or salts thereof, used in the mixture contained in the composition (C) of the present invention, in combination with the substances (a) and (c) and/or (d), is linear or branched; the hyaluronic acid is preferably in linear form.

Preferably, the mixture contained in said composition (C) according to the present invention comprises linear or branched hyaluronic acid, or salts thereof, having molecular weight comprised from 400 to 900 kDa, preferably from 600 to 800 kDa; the hyaluronic acid is preferably in linear form.

More preferably, the mixture contained in said composition (C) according to the present invention comprises sodium hyaluronate having a molecular weight comprised from 600 to 800 kDalton (CAS No. 9067-32-7).

In a preferred embodiment, the composition (C) of the present invention further comprises at least one other glycosaminoglycan (GAG), or a salt thereof, in addition to the hyaluronic acid; more preferably, said GAG is a salt of chondroitin; even more preferably, said GAG is the substance (d) chondroitin sulphate.

The chains of chondroitin, or of the derivatives thereof such as sulphate, are branchless polysaccharides of variable length containing two alternating monosaccharides: D-glucuronic acid (GlcA) and N-acetyl-D-galactosamine (Gal- NAc), wherein the residues of GlcA can be epimerised into L-iduronic acid (the resulting disaccharide is called Dermatan sulphate).

It is known from the Merck Index (14-th edition) that chondroitin sulphate is a generic term that indicates a polymer having an average molecular weight of about 50,000 Da.

There exist various forms of chondroitin sulphate, such as, for example, chondroitin 4-sulphate A [CAS No. 24967-93-9], the sodium salt thereof [CAS No. 9082-07-9] or the disodium salt thereof [CAS No. 39455-18-0]. The form chondroitin 6-sulphate (chondroitin sulphate C) also exists—CAS No. 25322-46-7.

In the context of the present invention, it is envisaged to use one of the above-mentioned forms of chondroitin sulphate (d) in combination with the substances (a), (b) and (c) and said chondroitin (d) is chicken chondroitin.

Preferably, the chondroitin sulphate (optionally in the form of a sodium salt) in the composition for use according to the present invention has an average molecular weight that depends on the specific form of chondroitin used.

It has been found that the administration of the liquid composition (C) according to the invention, also comprising chondroitin sulphate, has the effect of further reducing the symptoms associated with gastroesophageal reflux, practically in the absence of undesirable effects.

The chondroitin sulphate in the composition (C) of the invention preferably derives from chicken, fish (e.g. shark chondroitin sulphate, CAS number 9082-07-9), bovines or swine or is of vegetable origin; more preferably, the chondroitin sulphate, or salts thereof, used in the composition of the present invention derives from chicken. By way of non-limiting example, the chondroitin sulphate in the composition according to the present invention may be chicken chondroitin sulphate sodium salt and contain, relative to the total weight of chondroitin sulphate sodium salt, at least 91.5% by weight of chondroitin sulphate and no more than 8.5% by weight of sodium, it may have a protein content no greater than 6% by weight and have a pH comprised from 5.5 to 7.5 and/or a specific rotation comprised from 10° to 20° (for example determined with the methods of the European Pharmacopoeia 7.0).

In a preferred embodiment, the liquid composition (C) according to the present invention comprises a mixture which comprises or, alternatively, consists of:
  (a) an *Aloe vera* gel in an amount comprised from 0.1 to 0.5%;
  (b) a hyaluronic acid in an amount comprised from 0.1 to 0.5%;
  (c) a honey in an amount comprised from 10 to 40%; and
  (d) a salt of chondroitin sulphate, preferably a sodium salt, if present, in an amount comprised from 1 to 4%; wherein all the amounts are by weight relative to the total weight of (C).

In a preferred embodiment, the liquid composition (C) of the present invention comprises, per 100 ml of (C):
  (a) an *Aloe vera* gel in an amount comprised from 150 to 300 mg;
  (b) a hyaluronic acid in an amount comprised from 100 to 300 mg;
  (c) a honey 20-30 g; and, optionally,
  (d) a salt of chondroitin sulphate 2-3 g.

In a more preferred embodiment, the liquid composition (C) comprises, per 100 ml of (C):
  (a) lyophilised *aloe vera* gel 0.25 g;
  (b) hyaluronic acid 0.2 g;
  (c) honey 25 g.

In another more preferred embodiment, the liquid composition (C) comprises, per 100 ml of (C):
  (a) lyophilised *aloe vera* gel: 0.25 g;
  (b) hyaluronic acid: 0.2 g;
  (c) honey: 25 g;
  (d) a salt of chondroitin, preferably chondroitin sulphate: 2.5 g.

The liquid composition (C) according to the present invention, in addition to the component (a)-(c) and, optionally, (d), can further comprise other active ingredients such as, by way of non-limiting example, anti-inflammatory agents, oral cavity disinfectants, antacids and mixtures thereof.

The composition (C) as defined above can further comprise at least one excipient, or additive, i.e. a substance devoid of therapeutic activity, suitable for pharmaceutical or food use. In the context of the present invention the acceptable ingredients for pharmaceutical or food use comprise all the auxiliary substances known to the person skilled in the art and suitable for the preparation of liquid forms for oral administration, such as, by way of non-limiting example, diluents, solvents (including water, glycerine, ethyl alcohol), solubilisers, thickeners, sweeteners, flavourings, colourants, lubricants, surfactants, antimicrobials, antioxidants, preservatives, pH stabilising buffers and mixtures thereof. Non-limiting examples of such substances are maltodextrins, phosphate buffers, bases such as sodium hydroxide, xanthan gum, guar gum, fructose, and natural or artificial flavourings.

In one aspect, the present invention provides a medical device comprising the composition (C) as defined above.

In the context of the present invention, the term "medical device" is used with the meaning according to Italian Legislative Decree no. 46 of 24 Feb. 1997, i.e. it indicates a substance or another product, whether used alone or in combination, intended by the manufacturer to be used for human beings for the purpose of diagnosis, prevention, monitoring, treatment or alleviation of disease, and which does not achieve its principal intended action in or on the human body for which it is intended by pharmacological, immunological or metabolic means, but which may be assisted in its function by such means.

By way of non-limiting example, said medical device can be in the form of a syrup, liquid or semi-solid preparation, gel, suspension, solution, two-phase liquid system and equivalent forms.

Preferably, the medical device according to the invention is in the form of a syrup.

In one aspect, the present invention provides a composition comprising a mixture or an association or a combination which comprises or, alternatively, consists of:
  (a) *Aloe vera* gel;
  (b) hyaluronic acid; and
  (c) honey
for use in the treatment and/or in the prevention of gastroesophageal reflux disease, wherein said use comprises the administration of (a), (b) or (c) to a subject in any sequence or simultaneously.

For the sake of clarity, in order to achieve the object of the present invention, (a), (b) and (c) can be also administered separately and in any order but, preferably, (a), (b) and (c) are administered to a subject simultaneously, and even more preferably in a single composition so as to obtain a more rapid effect and facilitate administration.

Preferably, said combination according to the present invention further comprises a salt of chondroitin, preferably of chondroitin sulphate, such as the sodium salt of chondroitin sulphate. The source of the chondroitin is preferably chicken.

The following examples are provided in order to illustrate some embodiments of the invention, without any intention of limiting the scope thereof.

EXAMPLES

Example 1

A composition (C) according to the invention was prepared in the form of a syrup (total volume of 100 ml) comprising the following ingredients:

| | |
|---|---|
| Lyophilised *Aloe vera* gel (a): | 0.25 g |
| Sodium hyaluronate (b): | 0.23 g |
| Honey (c): | 25 g |
| Fructose: | 23.8 g |
| Hydroxypropyl methylcellulose: | 3 g |
| Benzoates (preservatives): | 0.15 g |
| Flavourings: | 0.3 g |
| Thickener: | 0.1 g |
| Purified water: | q.s. to 100 ml |

Example 2

A composition (C) according to the invention was prepared in the form of a syrup (total volume of 100 ml) comprising the following ingredients:

| | |
|---|---|
| Lyophilised *Aloe vera* gel (a): | 0.25 g |
| Sodium hyaluronate (b): | 0.23 g |
| Honey (c): | 25 g |
| Chondroitin sulphate sodium (d): | 2.8 g |
| Fructose: | 23.8 g |
| Hydroxypropyl methylcellulose: | 3 g |
| Benzoates (preservatives): | 0.15 g |
| Flavourings: | 0.3 g |
| Thickener: | 0.1 g |
| Water: | q.s. to 100 ml |

Example 3

A composition (C) according to the invention was prepared in the form of a syrup (total weight 100 g) comprising the following ingredients:

| | |
|---|---|
| Lyophilised *Aloe vera* gel (a): | 0.21 g |
| Sodium hyaluronate (b): | 0.24 g |
| Honey (c): | 21 g |
| Chondroitin sulphate sodium (d): | 2.3 g |
| Fructose: | 6.2 g |
| Potassium/dipotassium phosphate buffer | 2.1 g |
| Sodium hydroxide | 0.15 g |
| Benzoates (preservatives): | 0.15 g |
| Xanthan gum | 0.25 g |
| Flavourings: | 0.3 g |
| Maltodextrins | 11.6 g |
| Thickener (guar flour) | 0.2 g |
| Water: | 55 g |
| Other excipients: | q.s. to 100 g |

The compositions of examples 1, 2 and 3 were orally administered to subjects affected by gastroesophageal reflux disease (GERD), diagnosed through endoscopic analysis.

All subjects reported an improvement in the symptoms associated with GERD, while no significant side effects were caused.

In the embodiment of the above-referred formulation (liquid composition (C)), the aforesaid invention lends itself to being used in subjects of all ages, from newborns to the elderly.

The liquid composition (C) of the present invention (which comprises a mixture which comprises or, alternatively, consists of (a), (b), (c) and/or (d)): is preferably an association (mixture) of Chondroitin Sulphate, Hyaluronic acid, *Aloe* and Honey, endowed with the following properties:

Hydrating, moistening, lubricating, viscosity enhancing, film-forming and protective, with a barrier effect due to the formation of a viscous layer that coats the esophageal mucosa by adhering to it ("gripping" action), thus exerting a barrier action useful for preventing the contact of the mucosa itself with external agents, and contributing to alleviating irritative states and favouring, therefore, a proper trophism and correct functionality. By virtue of such effects, the aforesaid invention is capable of exerting a trophic, anti-inflammatory, analgesic (pain-killing), reparative (cicatrising), restorative and re-epithelising (it favours tissue regeneration) action.

Emollient and soothing effect, preferably on the epithelium and the oral-pharyngeal-laryngeal and esophageal mucosa, useful for providing relief of the most common symptoms of GERD and calming coughs and other related symptoms. By virtue of such effects, the aforesaid invention is capable of exerting a refreshing, balsamic, calming and cough-sedating action.

It protects the tissue of the damaged gastroesophageal tract and favours the regeneration of the damaged mucosa, and is useful for preventing the damage induced by the irritating action due, in particular, to contact with the substances regurgitated in the gastroesophageal tract. By virtue of such effects, the aforesaid invention is capable of exerting a gastroprotective action.

The liquid composition (C) comprising a mixture which comprises or, alternatively, consists of (a), (b), (c) and/or (d) is in the form of a solution or syrup or sachets and enables better contact of the individual components/substances with the oral-pharyngeal-laryngeal-esophageal wall, favouring the protection, lubrication and repair thereof:

Chondroitin-Sulphate adheres to the gastro-esophageal mucosa and protects it by effectively isolating it from the attack of gastric juices;

Hyaluronic acid, in combination with the adhesive properties of Chondroitin Sulphate, protects the damaged gastric tissue and favours its regeneration;

Honey exerts a soothing, hydrating and protective action due to the formation of a film that coats the esophageal mucosa, with a barrier action, protecting the irritated mucosa and hydrating it, thus alleviating the sensation of pain. Furthermore, by acting at the level of the oropharyngeal mucosa, it alleviates the throat irritations provoked by the acidity of the reflux;

*Aloe*, together with the properties of the honey, exerts a refreshing, soothing and protective action on the esophageal mucosa, providing a barrier effect. In fact, aloe, thanks to its content of mucopolysaccharides, possesses gastroprotective properties, because by distributing themselves over the mucosa of the stomach, they form a sort of film that protects the entire gastric tract from acids or irritant agents that would alter its correct functioning.

Preferred intended uses of the aforesaid liquid composition (C) comprising a mixture which comprises or, alternatively, consists of (a), (b), (c) and/or (d) are: as an adjuvant for the symptomatic treatment of gastroesophageal reflux disease; or for use in a preventive and/or curative action against: (i) lesions of the oral cavity (e.g. tongue and palate) and of the pharyngeal-laryngeal-esophageal tract; (ii) mucositis; (iii) aphthae and/or aphthoid lesions.

The present invention relates to a liquid composition (C) which comprises a combination or an association or a mixture which comprises or, alternatively, consists of: (a) *Aloe vera* gel; (b) hyaluronic acid; and (c) honey and, optionally, (d) chondroitin sulphate or a salt thereof, preferably a sodium salt, for use as an adjuvant for the symptomatic treatment of gastroesophageal reflux disease; or for use in a preventive and/or curative treatment against: (i) lesions of the oral cavity (e.g. tongue and palate) and of the pharyngeal-laryngeal-esophageal tract; (ii) mucositis; (iii) aphthae and/or aphthoid lesions, wherein said use comprises the administration of (a), (b), (c) and/or (d) to a subject in any sequence or simultaneously.

Experimental Trials

In Vitro Test

The model used was Reconstituted Human Esophageal Epithelium, produced by Episkin °, Lyons (F)

Film-Forming/Mucoadhesive/Protective Action

The time of contact with the esophageal mucosa was 15 min (time for stabilisation of the deposit of products at the level of the mucosa) for all protocols. The time was extended to 1 h after elimination of the excess of the residual volume.

The following series of esophageal tissues (studies conducted in biological triplicate, except for SEM) were prepared in the various protocols:
1. negative control—neutral environment
2. negative control—acidic environment
3. positive control—neutral environment (Vaseline)
4. positive control—acidic environment (Vaseline)
5. treated with the aforesaid invention in an acidic environment
6. treated with the aforesaid invention in a neutral environment The products (100 μL) dispersed in saline solution were applied for 15 minutes and after removal of the excess for up to 1 h on the surface of the esophageal epithelium at a temperature of 32° C.; then, without removing it, 100 μL of a 0.5%/0.5 cm² solution of caffeine and 1 mg caffeine/cm' (in an acidic or neutral solution) were applied. During this period the receptor fluid below the insert was represented by a saline solution.

The receptor fluids were recovered at 15 min, 1 h and 2 h in the basolateral compartment and subsequently analysed for the content of caffeine with the HPLC technique. The tissues were then used to carry out a Lucifer Yellow (LY) assay to confirm the integrity and permeability of the barrier. Lucifer yellow is a fluorescent marker impermeable to the cell membrane. The LY solution was applied topically and the transport of LY was evaluated as passage into the basolateral compartment. The reading of the fluorescent substance was measured with a spectrofluorometer with an exciting wavelength of 428 nm and emission of 525 nm. The % effectiveness was calculated relative to the amount of caffeine found in the receptor fluid of the negative control (not treated=100% passage).

Anti-Inflammatory Action

An abrasion or a treatment with acids was carried out on the previously described model so as to induce and simulate the loss of continuity in the mucosa damaged by lesions due to acidic reflux and thereby provoke inflammation. The gene expression in the injured/inflamed model was then assessed by qRT-PCR on:
β-defensin type 2 (natural antimicrobial peptide),
involucrin,
TNF-alpha,
TLR-2.

Re-Epithelising/Reparative Action

On the same model of esophageal epithelium, a study in biological triplicate was conducted for each series.
one series was not injured and served as a negative control
an injured series was treated with saline solution and served as a positive control
an abrasion/lesion was applied on one series, which was treated with the aforesaid invention 1 h after the lesion had been created At defined times t=6 h and t=24 h the integrity of the barrier was measured with TEER and the release of LDH in the medium was measured.

Specifically, a surface abrasion/acid pH treatment was applied on the surface in order to induce and simulate the loss of continuity of the mucosa damaged by lesions due to acid reflux. Abrasions result in a reduction in electrical resistance (TEER) and an increase in the release of LDH and loss of connection of the cells of the surface epithelium.

At the end, the tissues were used for biotin marking with an immunohistochemical technique, which distinguishes the permeable parts of the tissue from the non-permeable ones, which therefore, have an intact barrier function.

Finally, the following factors were also assessed:
TGF (Transforming Growth Factor)-beta 1 and TGF-beta 2, which play an important role in controlling cell proliferation and differentiation.

Description of Parameters

Measurement of TEER (Transepithelial Electrical Resistance)

Transepithelial electrical resistance (TEER) is a direct measurement of the functionality of the barrier of epithelial tissues: it reflects the global resistance of the tissue due both to its thickness and structure, since it reflects the integrity of intercellular contacts at the level of the tight junctions which oppose the penetration of external substances.

Release of LDH and Barrier Permeability

The enzyme lactate dehydrogenase (LDH) is normally present in the cytoplasm and cannot be found outside cells except as a result of damage to the cell membrane. A histological and complementary immunohistochemical analysis make it possible to visualise the interaction of the product with living tissue and the structure of the proteins of tight junctions (zonulin-1 and occludin), which are essential for maintaining the barrier intact.

Embodiments FRn of the present invention are set forth below and are all part of the subject matter of the present invention.

FR1. A liquid composition (C) comprising the following components/substances: (a) *Aloe vera* gel; (b) hyaluronic acid, or a salt thereof; and (c) honey.

FR2. The composition (C) according to FR 1, wherein the hyaluronic acid has a molecular weight comprised from 400 to 900 kDa, preferably from 600 to 800 kDa.

FR3. The composition (C) according to either of the preceding embodiments FR1 or FR2, further comprising:
(d) a salt of chondroitin, preferably of chondroitin sulphate, as a chondroitin sulphate sodium salt.

FR4. The composition (C) according to one of the preceding embodiments FR1-FR3, wherein the *Aloe vera* gel is a lyophilised inner leaf gel.

FR5. The composition (C) according to one of the preceding embodiments FR1-FR4 wherein:
(a) is in an amount comprised from 0.1 to 0.5%
(b) is in an amount comprised from 0.1 to 0.5%
(c) is in an amount comprised from 10 to 40%; and
(d), if present, is in an amount comprised from 1 to 4%, wherein all of the amounts are in weight relative to the total weight of (C).

FR6. The composition (C) according to one of the preceding embodiments FR1-FR5, comprising, per 100 ml of (C):
(a) in an amount comprised from 150 to 300 mg;
(b) in an amount comprised from 100 to 300 mg;
(c) 20-30 g; optionally
(e) 2-3 g.

FR7. A medical device comprising the composition (C) according to any one of the preceding embodiments FR1-FR6.

FR8. A combination of: (a) *Aloe vera* gel; (b) hyaluronic acid; and (c) honey and, optionally, (d) chondroitin sulphate or a salt thereof, preferably a sodium salt, for use in the treatment and/or in the prevention of gastroesophageal reflux disease, wherein said use comprises the administration of (a), (b) and (c) to a subject in any sequence or simultaneously.

FR9. The combination for use according to the embodiment FR 8, wherein said use comprises the administration of a), b) and c) simultaneously, preferably in a single composition.

FR10. The composition (C) according to at least one of the preceding embodiments FR1-FR6, having one of the following three compositions:

Composition 1:
Lyophilised *Aloe vera* gel (a): 0.25 g
Sodium hyaluronate (b): 0.23 g
Honey (c): 25 g
Fructose: 23.8 g
Hydroxypropyl methylcellulose: 3 g
Benzoates (preservatives): 0.15 g
Flavourings: 0.3 g
Thickener: 0.1 g
Purified water: q.s. to 100 ml Composition 2:
Lyophilised *Aloe vera* gel (a): 0.25 g
Sodium hyaluronate (b): 0.23 g
Honey (c): 25 g
Chondroitin sulphate sodium (d): 2.8 g
Fructose: 23.8 g
Hydroxypropyl methylcellulose: 3 g
Benzoates (preservatives): 0.15 g
Flavourings: 0.3 g
Thickener: 0.1 g
Water: q.s. to 100 ml Composition 3:
Lyophilised *Aloe vera* gel (a): 0.21 g
Sodium hyaluronate (b): 0.24 g
Honey (c): 21 g
Chondroitin sulphate sodium (d): 2.3 g
Fructose: 6.2 g
Potassium/dipotassium phosphate buffer: 2.1 g
Sodium hydroxide: 0.15 g
Benzoates (preservatives): 0.15 g
Xanthan gum: 0.25 g
Flavourings: 0.3 g
Maltodextrins: 11.6 g
Water: 55 g
Other excipients: q.s. to 100 g

The invention claimed is:

1. An orally-administered liquid formulation comprising an *Aloe vera* gel, a hyaluronic acid or a salt thereof and a honey in therapeutically effective amounts for treating gastroesophageal reflux disease.

2. The orally-administered liquid formulation of claim 1, wherein the hyaluronic acid has a molecular weight from 400 to 900 kDa.

3. The orally-administered liquid formulation of claim 2, wherein the hyaluronic acid has a molecular weight from 600 to 800 kDa.

4. The orally-administered liquid formulation of claim 1, wherein the *Aloe vera* gel is a lyophilised inner leaf gel.

5. The orally-administered liquid formulation of claim 1, wherein the *Aloe vera* gel is present in an amount from 0.1% to 0.5%, the hyaluronic acid or a salt thereof is present in an amount from 0.1% to 0.5%, and the honey is present in an amount from 10 to 40%, wherein all of the amounts are in weight relative to a total weight of the formulation.

6. The orally-administered liquid formulation of claim 1, further comprising one or more pharmaceutical or food grade additives, excipients or combinations thereof.

7. The orally-administered liquid formulation of claim 6, wherein the one or more pharmaceutical or food grade additives or excipients comprise one or more solvents, one or more solubilizers, one or more thickeners, one or more sweeteners, one or more flavourings, one or more colorants, one or more lubricants, one or more surfactants, one or more antimicrobials, one or more antioxidants, one or more preservatives, one or more pH stabilising buffers or mixtures thereof.

8. The orally-administered liquid formulation of claim 7, wherein the one or more solvents comprise water, glycerine, ethyl alcohol or mixtures thereof.

9. The orally-administered liquid formulation of claim 6, wherein the formulation comprises maltodextrins, phosphate buffers, sodium hydroxide, xanthan gum, guar gum, fructose or mixtures thereof.

10. The orally-administered liquid formulation of claim 9, further comprising a chondroitin sulphate or a salt thereof.

11. The orally-administered liquid formulation of claim 10, wherein the salt of chondroitin sulphate is chondroitin sulphate sodium or chondroitin sulphate disodium.

12. The orally-administered liquid formulation of claim 10, wherein the chondroitin sulphate or a salt thereof is present in an amount from 1% to 4% by weight relative to the total weight of the formulation.

13. The orally-administered liquid formulation of claim 10, wherein per 100 ml of the formulation comprises:
the *Aloe vera* gel in an amount from 150 to 300 mg;
the hyaluronic acid or the salt thereof in an amount from 100 to 300 mg;
the honey in an amount from 20 g to 30 g; and
optionally the chondroitin sulphate or a salt thereof in an amount from 2 g to 3 g.

14. The orally-administered liquid formulation of claim 10, having the following components:

| | |
|---|---|
| lyophilised Aloe vera gel: | 0.25 g |
| sodium hyaluronate: | 0.23 g |
| honey: | 25 g |
| fructose: | 23.8 g |
| hydroxypropyl methylcellulose: | 3 g |
| benzoates: | 0.15 g |
| flavourings: | 0.3 g |
| thickener: | 0.1 g |

| | |
|---|---|
| purified water: | q.s. to 100 ml. |

15. The orally-administered liquid formulation of claim 10, having the following components:

| | |
|---|---|
| lyophilised Aloe vera gel: | 0.25 g |
| sodium hyaluronate: | 0.23 g |
| honey: | 25 g |
| chondroitin sulphate sodium: | 2.8 g |
| fructose: | 23.8 g |
| hydroxypropyl methylcellulose: | 3 g |
| benzoates: | 0.15 g |
| flavourings: | 0.3 g |
| thickener: | 0.1 g |
| water: | q.s. to 100 ml. |

16. The orally-administered liquid formulation of claim 10, having the following components:

| | |
|---|---|
| lyophilised Aloe vera gel: | 0.21 g |
| sodium hyaluronate: | 0.24 g |
| honey: | 21 g |
| chondroitin sulphate sodium: | 2.3 g |
| fructose: | 6.2 g |
| potassium/dipotassium phosphate buffer: | 2.1 g |
| sodium hydroxide: | 0.15 g |
| benzoates: | 0.15 g |
| xanthan gum: | 0.25 g |
| flavourings: | 0.3 g |
| maltodextrins: | 11.6 g |
| water: | 55 g |
| other excipients: | q.s. to 100 g. |

17. A medical device comprising the orally-administered liquid formulation of claim 1.

18. The medical device of claim 17, wherein the medical device is in the form of a syrup, liquid, semi-solid preparation, gel, suspension, solution or two-phase liquid system.

19. An orally-administered liquid formulation comprising an *Aloe vera* gel, a hyaluronic acid or a salt thereof, a honey and a salt of chondroitin in therapeutically effective amounts for treating (i) lesions of the oral cavity and of the pharyngeal-laryngeal-esophageal tract; (ii) mucositis; and/or (iii) aphthae and/or aphthoid lesions, the formulation further comprising one or more food or pharmaceutical grade additives, excipients or combinations thereof.

20. The orally-administered liquid formulation of claim 19, wherein the *Aloe vera* gel is present in an amount from 0.1% to 0.5%, the hyaluronic acid or a salt thereof is present in an amount from 0.1% to 0.5%, the honey is present in an amount from 10 to 40%, and the salt of chondroitin is present in an amount from 1 to 4%, wherein all of the amounts are in weight relative to the total weight of the formulation.

* * * * *